(12) United States Patent
Dvir

(10) Patent No.: US 12,274,887 B2
(45) Date of Patent: Apr. 15, 2025

(54) PERSONAL WEARABLE MEDICAL EMERGENCY DEVICE

(71) Applicant: Yossi Dvir, Petach Tikva (IL)

(72) Inventor: Yossi Dvir, Petach Tikva (IL)

(*) Notice: Subject to any disclaimer, the term of this patent is extended or adjusted under 35 U.S.C. 154(b) by 631 days.

(21) Appl. No.: 17/600,155

(22) PCT Filed: Apr. 1, 2020

(86) PCT No.: PCT/IB2020/053114
§ 371 (c)(1),
(2) Date: Sep. 30, 2021

(87) PCT Pub. No.: WO2020/202042
PCT Pub. Date: Oct. 8, 2020

(65) Prior Publication Data
US 2022/0152407 A1    May 19, 2022

Related U.S. Application Data

(60) Provisional application No. 62/827,204, filed on Apr. 1, 2019.

(51) Int. Cl.
A61N 1/39      (2006.01)
A61N 1/04      (2006.01)
A61N 1/36      (2006.01)

(52) U.S. Cl.
CPC .......... *A61N 1/3904* (2017.08); *A61N 1/046* (2013.01); *A61N 1/0484* (2013.01); *A61N 1/0492* (2013.01); *A61N 1/36031* (2017.08); *A61N 1/3918* (2013.01); *A61N 1/3925* (2013.01); *A61N 1/395* (2013.01); *A61N 1/3968* (2013.01); *A61N 1/3975* (2013.01)

(58) Field of Classification Search
CPC .. A61N 1/3904; A61N 1/36031; A61N 1/046; A61N 1/0484; A61N 1/0492; A61N 1/3918; A61N 1/3925; A61N 1/395; A61N 1/3968; A61N 1/3975
See application file for complete search history.

(56) References Cited

U.S. PATENT DOCUMENTS

| | | | |
|---|---|---|---|
| 2003/0171797 A1* | 9/2003 | Nova ..................... | A61B 5/266 607/142 |
| 2011/0022025 A1* | 1/2011 | Savoie .............. | A61M 5/14248 604/151 |
| 2014/0085081 A1* | 3/2014 | Brown ................. | A61N 1/3993 607/6 |
| 2015/0335244 A1* | 11/2015 | Guiney ................. | A61B 5/686 600/510 |
| 2016/0303371 A1* | 10/2016 | Whiting .............. | A61B 5/6831 |
| 2016/0325107 A1* | 11/2016 | Park ..................... | A61N 1/3621 |
| 2017/0246466 A1* | 8/2017 | Murphy .............. | A61N 1/3975 |
| 2018/0243575 A1* | 8/2018 | Freeman ............. | A61N 1/3918 |

* cited by examiner

*Primary Examiner* — Mallika D Fairchild
*Assistant Examiner* — Thien Jason Tran
(74) *Attorney, Agent, or Firm* — Rivka Friedman

(57) ABSTRACT

A personal wearable emergency medical treatment device, including: a first housing unit including an control unit for an automatic defibrillator device; at least two, and preferably three, electrodes in electrical communication with the housing unit; wherein the electrodes are adapted to be positioned in proximity to a human body at preselected positions selected for monitoring for heartbeat abnormalities and providing electric pulses to the human body.

34 Claims, 12 Drawing Sheets

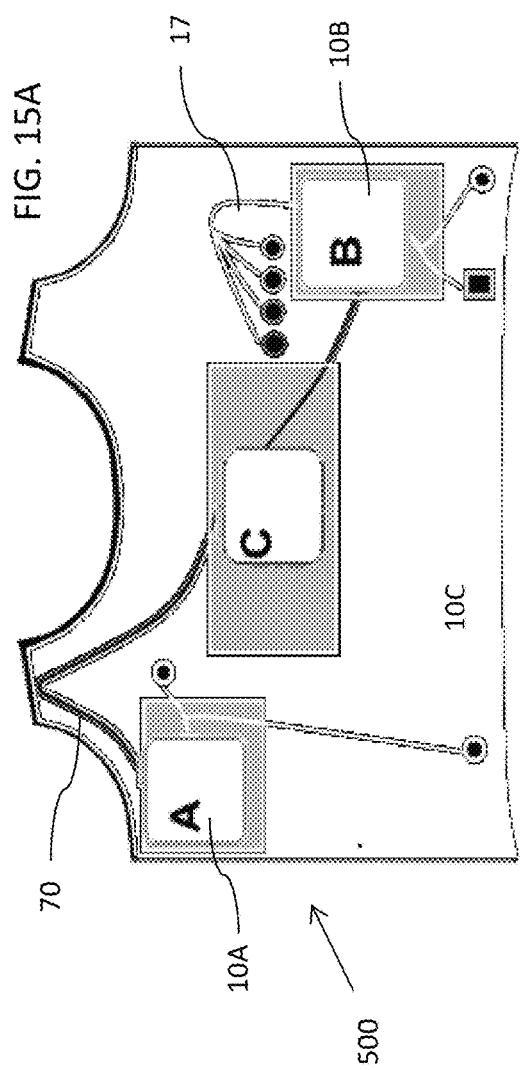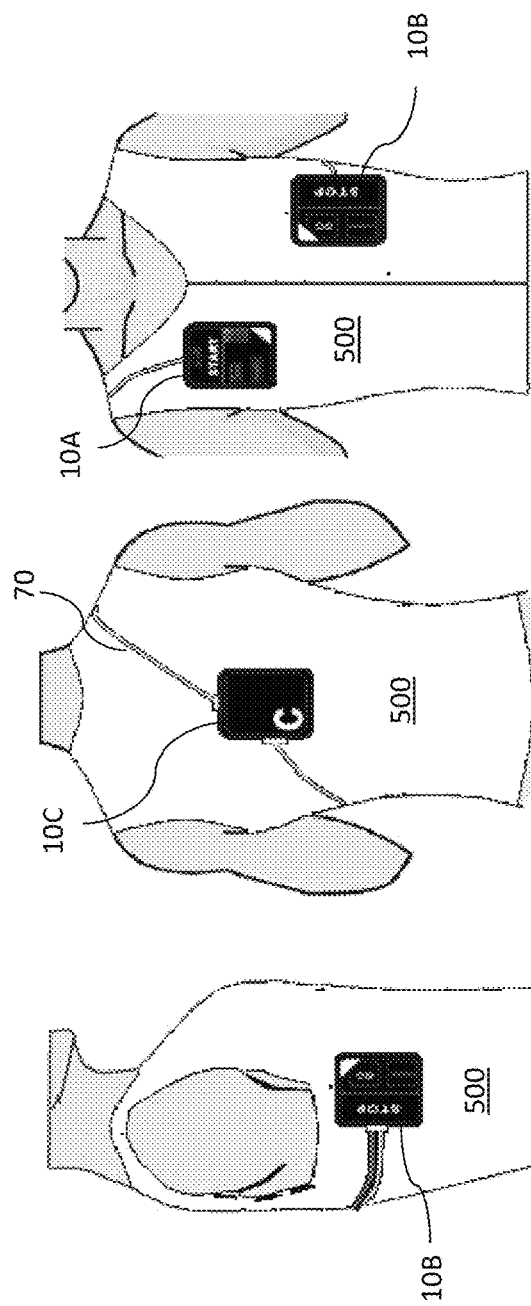

PERSONAL WEARABLE MEDICAL EMERGENCY DEVICE

FIELD OF THE INVENTION

The present invention relates to a personal wearable medical emergency device which combines multiple devices all for the purpose of providing personal emergency medical treatment to the wearer of the device. This invention relates to Automatic External Defibrillator (AED) Systems in general, heart monitoring technology, ultrasound technology and injectable medicine technology.

BACKGROUND OF THE INVENTION

An Automatic External Defibrillator (AED) is a portable electronic device that can be constantly connected to a patient and which automatically diagnoses cardiac arrhythmias such as ventricular fibrillation and ventricular tachycardia of a patient. The AED provides a fast response by delivering an electric pulse at a time of need, defibrillating the cardiac arrhythmias to a normal state, thereby stopping the arrhythmia and allowing a cardio system to rebuild an effective rhythm.

A basic external defibrillator needs a battery to supply alternating current through the primary winding of transformer. This results in a high-voltage output from the secondary winding of transformer, which is captured by diode and stored in a capacitor. When it is desired to deliver a shock, switching by a switch or a FET transistor, thus delivering the high voltage and high current from capacitor to electrodes attached to the chest. A biphasic shock can also be delivered.

Another arrangement can be a network of diodes and capacitors to provide high voltage. Large capacitors can store large potential. Shock voltages range from 1400 to 4000 volts, and power is between 150 to 400 joules.

SUMMARY OF THE INVENTION

A system for monitoring vital signs of a live body includes an external device; and a portable monitoring device. The monitoring device includes an electrical circuit, which, in turn, includes a controller, data storage, and input ports. The electrical circuit is designed to read inputs and store data. The monitoring device further includes a number of sensors which are connected to the electrical circuit, each of the sensors detecting a property of the body. The device also includes defibrillation capability. The device further includes a mechanism for transferring stored data or received inputs to the inquiring device, further allowing the downloading of data and the setting or changing of one or more set-points. The monitoring device includes a housing for holding the electrical circuit and sensors, as well as the communication means, the defibrillator device and the power supply. Finally the portable monitoring device housing may be substitute with a skin patch.

According to the present invention there is provided a personal wearable emergency medical treatment device, including: a first housing unit including an control unit for an automatic defibrillator device; at least two electrodes in electrical communication with the housing unit; wherein the electrodes are adapted to be positioned in proximity to a human body at preselected positions selected for monitoring for heartbeat abnormalities and providing electric pulses to the human body.

According to further features in preferred embodiments the device further includes a third electrode in electrical communication with the housing unit. According to still further features in the described preferred embodiments one of the at least three electrodes is housed in the first housing unit. According to further features the device further includes further at least one additional housing unit, and wherein at least two of the three electrodes each respectively housed in the housing units.

According to further features the electrodes are inserted into a garment adapted to be worn on the human body such that the electrodes are in proximity to the human body.

According to further features the device further includes a flexible ultrasound probe in electrical communication with the housing unit. According to further features the device further includes comprising an emergency medicine patch in electrical communication with the housing unit, the patch including a syringe, a needle mechanically coupled to the syringe, the syringe adapted to store therein a medicament; and an actuator for expelling the medicament via the needle upon actuation by a signal sent from the housing unit.

According to further features the device is configured to be in wireless or wired communication with an external device. According to further features the device is capable of wirelessly receiving protocol updates direct from the external device. According to further features the device includes an application to be downloadable by the external device or from the internet.

According to further features the device has selectable dual functions, automatic and semi-automatic functioning modes according.

According to further features the device is configured to be charged and for multi-use. According to further features the device is for a plurality of operating modes. According to further features the operating modes include at least the modes of emergency, detection, children, and wearable. According to further features the wearable mode is a Go-Mode, intended for 24 hours wearing of the device on the patient body. According to further features the at least one of the electrodes is intended for wearable mode and at least one of the electrodes is intended for emergency mode.

According to further features the device is configured to be modular and is capable of to be connected to at least one of: additional electrodes, additional sensors, and additional devices. According to further features the device is personally configurable according to a patient's medical information. According to further features the device is configured to deliver electric shocks of different magnitudes.

According to further features the device is configured to measure body indications selected from the group including: temperature, heart rate, respiration rate, and blood sugar ranges. Measuring the blood sugar ranges is done by an additional sensor connected to the device.

According to further features at least one of the electrodes has a different size relative to at least one other electrode, intended for different shock magnitude. According to further features the electrodes comprise a wearable patch adapted to be adhered to skin of the human body.

According to another embodiment there is provided an electrode for providing an electrical current, including: an electrical lead; and a contact surface, the contact surface including a plurality of distinct shock areas; wherein the electrode is configured to deliver different electric shock magnitudes by electrifying different the distinct shock areas of the electrode.

According to further features the contact surface includes: a first, inner shock area in electrical communication with the electrical lead via a first point of contact, and a second, outer shock area in electrical communication with the electrical lead via a second point of contact. According to further features each of the distinct shock areas is bordered by an insulation material. According to further features the electrode is embodied in an adhesive patch According to further features the different shock magnitudes are manually selectable by an operator or automatically set.

According to another embodiment there is provided a pouch for carrying the multi-functional device, further including a charging port, a transformer, a battery, charging sockets and/or indicators.

According to another embodiment there is provided a monitoring and docking station including: a charging station, a communication system and a backup battery adapted for use with the multi-functional device. According to further features the monitoring and docking station further includes wide area wireless communication capabilities.

BRIEF DESCRIPTION OF THE DRAWINGS

Various embodiments are herein described, by way of example only, with reference to the accompanying drawings, wherein:

FIG. 15A is a view of the inside of a wearable vest;

FIGS. 15B, 15C and 15D are optional embodiments of the vest 500, as worn on a body;

DESCRIPTION OF THE PREFERRED EMBODIMENTS

The principles and operation of multi-functional personal emergency medical device according to the present invention may be better understood with reference to the drawings and the accompanying description.

Figure 1:
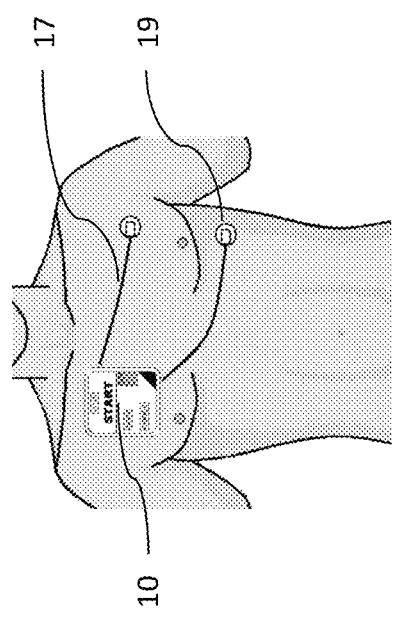
FIG. 1 is a view of a device of an embodiment of the present invention mounted over the chest.

FIG. 1 illustrates a device 10 of the instant invention mounted over the patient chest. Device 10 is a housing unit 10 that houses various components and provides the device with multifunctional capabilities. According to one aspect of the invention, device 10 functions as an ECG monitor. Electrodes 20, are additional to device 10. When placed encircling the heart, such an arrangement constitutes complete Einthoven triangle, allowing recording of Leads I, II, III, and AVF AVL AVR (see FIG. 3).

Figure 2:
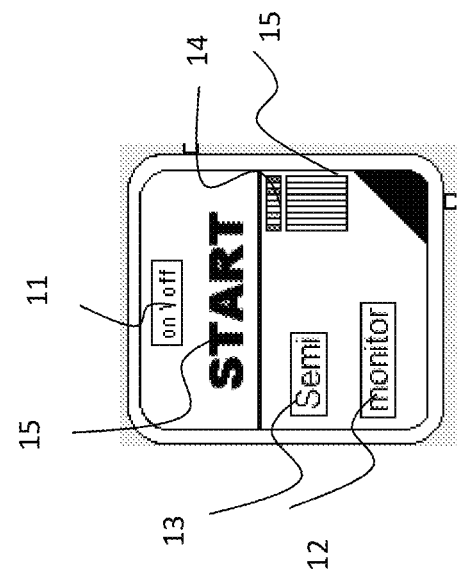
FIG. 2 is a view of the device of FIG. 1.

FIG. 2 depicts the housing unit/device 10 in further detail. Device 10 has an On/Off button 11, Monitor button 12, Semi 13, Electric shock status 14 and ECG output 15, and start button 16, which is used to start a sequence of electric shocks regardless of measured parameters. Buttons 12, 13, 16 are software assignable. Also buttons 12, 13, 16 can have dual use, as short press or long press will provide different result. An additional feature is pressing at least two of buttons 12, 13, 16, hence having 9 operating options out of 3 buttons, for example children mode and two possibilities therefore automatic and semi-automatic or emergency mode and two possibilities therefore automatic and semi-automatic. In an emergency mode and automatic possibility the device 10 automatically detects the heart rate and determines whether the patient's condition requires an electric shock. In that case the electric shock is given automatically. In a semi-automatic mode the electric shock is administered after a caregiver gives the instruction to device 10 to give an electric shock to the patient. ECG output 15, can also be used to indicate the system health, thus device 10 is in complete working order, indicating the battery status, as well as written or video instructions.

Figure 3:
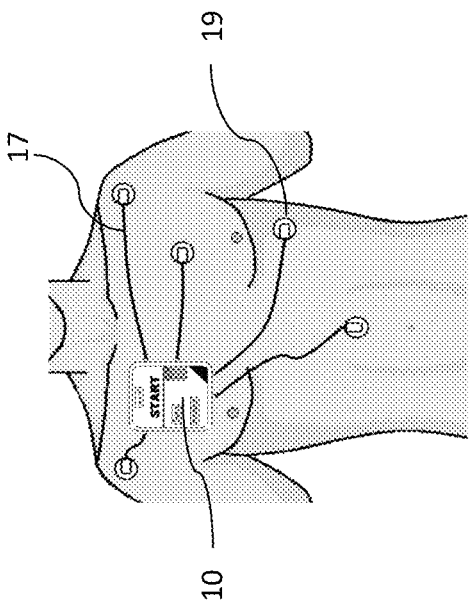
FIG. 3 is a view of the device of an embodiment of the present invention in communication with additional sensors and contacts.

FIG. 3 illustrates a single housing unit 10 (the same numbering is use to reference similar elements) with five additional leads 17 extending from the housing unit, each lead terminating in an electrode 19. The sixth electrode is housed within the housing unit 10. The six leads are arranged in an Einthoven triangle. Most of the electrodes serve as biosensors for providing ECG readings, heart rate and/or respiration rate. In preferred embodiments, at least some of the five electrodes are configured to provide an electrical pulse shock according to the current innovative method and system.

According to embodiments, defibrillator device of the instant innovation is configured to deliver cardiac electrical pulse to a patient, the defibrillator device including: a plurality of electrodes, of which at least two electrodes, and preferably three or more electrodes, are configured to deliver at least 50 joules to a living body, a plurality of electrodes for capturing cardiac signal data, for example the plurality of electrodes are configured to collect data from a multi-lead Einthoven triangle, an electrical circuit including a controller, data storage, and input ports, the electrical circuit being designed to read inputs and to store data, a plurality of sensors connected to the electrical circuit inputs, a communication port, for uploading and downloading data to other devices having a communication port, and an operating software, analyzing the captured cardiac signal data to determine whether a treatable cardiac arrhythmia is occurring.

According to preferred embodiments, the device is configured to: detect a cardiac event by observation of electrical signals captured using at least some of the electrodes; calculate a cardiac event rate relative to the detected cardiac event; analyze a correlation of the cardiac event relative to teachable patient cardiac output; and determine that the cardiac event has correlation to the teachable patient cardiac output and deliver at electrical pulse of at least 50 joules.

Although the first commercial defibrillator used a biphasic waveform for the treatment of ventricular fibrillation, commercial external defibrillators in the Western world adopted monophasic waveforms more than 45 years ago, and these have been used almost exclusively until the late 1990's. With biphasic shocks, the direction of current flow is reversed at some point near the halfway point of the electrical defibrillation cycle during the discharge from the defibrillator.

Low-energy biphasic shocks may be as effective as higher-energy monophasic shocks, albeit not in all situations. Evidence indicates that biphasic waveform shocks of 200 joules or less are safe and have equivalent or higher efficacy than damped sinusoidal waveform shocks of 200 J or 350 J. Atrial fibrillation (AF) studies indicate that 200 J biphasic energies are as effective as 360 J monophasic shocks. However, the emerging trend indicates that energies above 200 J may be required to increase effectiveness over monophasic. This may result in less damage to the myocardium and a reduced frequency of postshock contractility and dysrhythmias.

According to one aspect of the present innovation, there is provided three or more electrical leads/electrodes for delivering the electrical shocks. As discussed hereafter, the three-or-more electrode system is innovative as a stand-alone defibrillation or cardioversion device. Furthermore, the three or more electrode system can be implemented as one feature of the instant, multifunctional personal emergency medical device which provides an entire suite of automated emergency medicine to the user.

Referring to both of the heretofore mentioned embodiments, the plurality of electrodes can be used in two general types of implementation: The first type of implementation is to provide shocks from all the electrodes at once (are almost simultaneously). Usually the charge flows from one electrode to the other. With three electrodes (or more) two pulses (or more) can be administered simultaneously or almost simultaneously from two (or more) different locations to a third location, or from a first location to a second location and from a third location to a forth location.

The second type of implementation is a progressive shocking sequence. According to the second type of implementation, only two electrodes activate at any given time. The innovation is that if the personal device, which is also a monitoring device, decides that the first shock was ineffective (or insufficiently effective to correct the problem) a second set of electrodes performs a second shock. If the second shock is not successful a third shock is applied from a third position. The sequence progresses as necessary, each time from a different angle. The control unit is preprogrammed with the sequence. As diagnostic technology progresses, it will be possible to determine the best, most effective configuration for applying the shock or shocks.

Research has shown that biphasic defibrillation, as opposed to monophasic defibrillation, significantly decreases the energy level necessary for successful defibrillation, decreasing the risk of burns and myocardial damage. Authors have theorized that defibrillation from multiple sources (either in parallel or in sequence) will be at least as successful as current methods and likely more successful with further reduced energy usage. It is hypothesized that future research using the instant technology will prove the significant advantage of the multi-electrode approach disclosed herein over the legacy technology.

The current innovation is a paradigm shift from legacy defibrillator technology which uses two electrodes (positive and negative), where the current runs from one electrode to the other. All legacy defibrillator technology is based on two electrodes. One possible reasons for this is that all electrical appliances run off a current created between a positive and negative pole; so too with defibrillation. Another possible reason is that defibrillator paddles are used with external defibrillators (e.g. by EMTs and in hospitals). Seeing as a human being only has two hands, two paddles are used. The existing technology influenced the developing technology and all the defibrillators have remained with two electrodes, until now.

Figure 5:
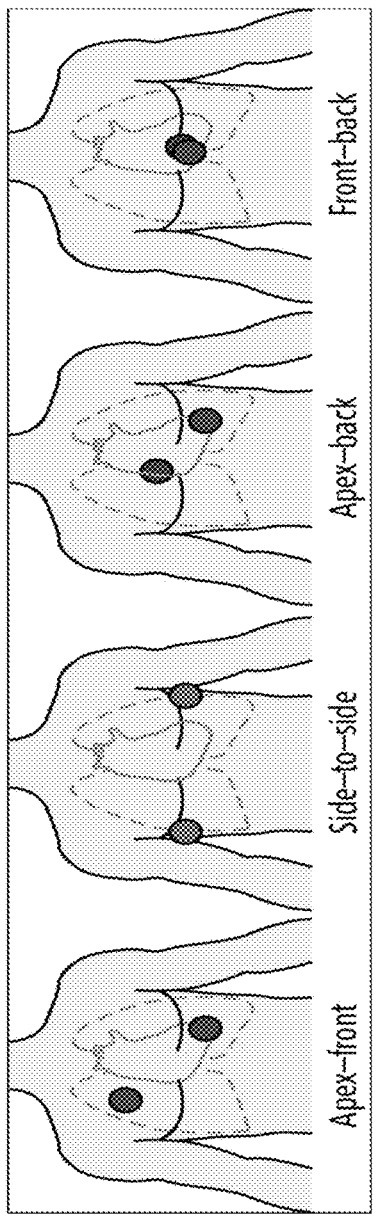
FIG. 5 is a prior art diagram of four positions for electrode placement in legacy defibrillators.

FIG. 5 is a prior art diagram of four standard positions for electrode placement in legacy defibrillators. From left to right, the first configuration is the well known anterior-apex scheme (also known as "apex-front" or "anterior-lateral" configuration). In this scheme, the anterior electrode is placed on the right of the patient, below the clavicle. The apex electrode is applied to the left side of the patient, just below and to the left of the pectoral muscle. This scheme works well for defibrillation and cardioversion, as well as for monitoring an ECG. The second configuration is the side-to-side configuration.

The third configuration is the apex-posterior scheme (or apex-back configuration). One electrode is placed over the apex. The other electrode is placed on the back, behind the heart in the region between the scapula.

The fourth configuration is the anterior-posterior scheme (or front-back configuration). One electrode is placed over the left precordium (the lower part of the chest, in front of the heart). The other electrode is placed on the back, behind the heart in the region between the scapula.

Figure 6:
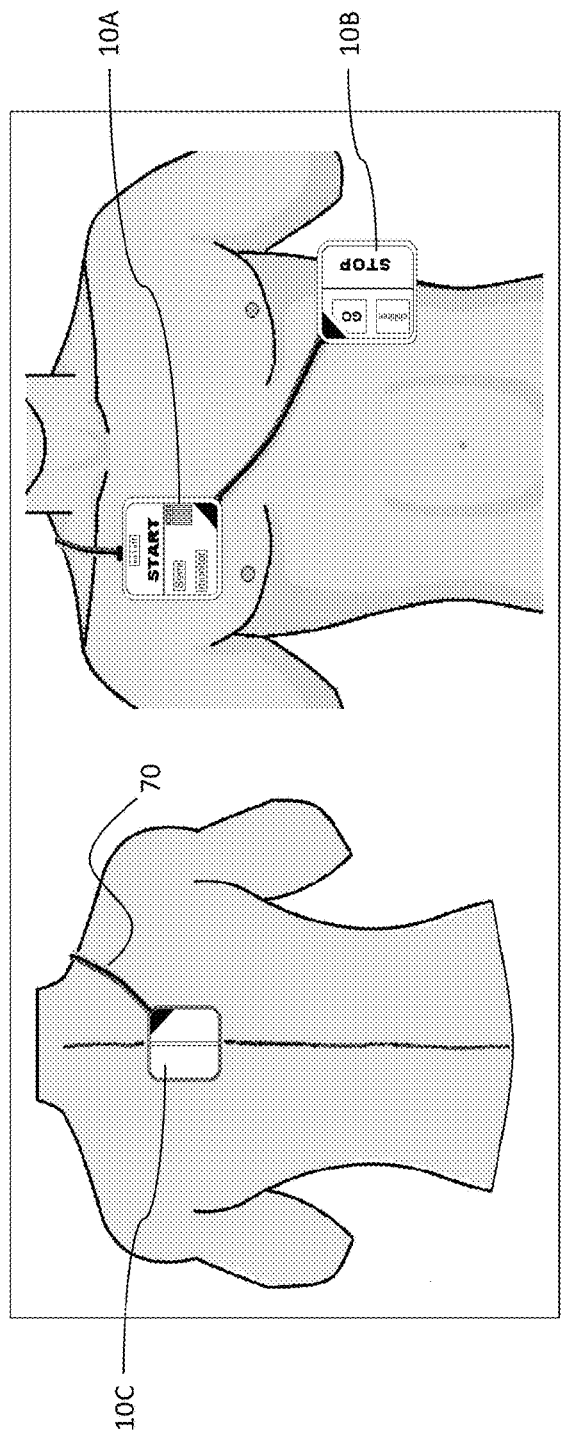
FIG. 6 is a view of two electrodes mounted on the front and an additional electrode mounted on a wearer's back.

FIG. 6 illustrates one embodiment of the instant three-electrode configuration. On the right hand side of the figure is a diagram of the front of an upper body of a person. Two housing units of the instant innovative system are depicted, in contact with the body. A first housing unit 10A is located in the "anterior" position and a second housing unit 10B is located in the "apex" position. On the left hand side of the figure is a diagram of the back of the same upper body. A third housing unit 10C is located in the "posterior" position (between the scapula), in electrical contact with the skin of the body. A cable equivalent communication 70 is used to separate devices 10, each one of them constitutes an electrode in a system composed of three devices 10 and cable equivalent 70. Cable equivalent 70 can be used to conduct power in case of defibrillation, or conduct communication between devices 10, or both. Lead 17 may or may not have the capabilities of cable 70.

The housing units can be attached to the skin using any medium or apparatus known in the art, for example, the housing unit can be embodied in a "patch" lined on the undersurface with a layer of bio-adhesive material. Each housing unit includes, inter alia, an electrode for administering an electrical shock. The instantly depicted configuration is a combination of the apex-back and apex-front standard configurations.

It is made clear that the depicted configuration is only one of a plurality of configurations that are included within the scope of the instant innovation. Furthermore, additional housing units and/or electrodes can be attached to the personal emergency medical device system.

Throughout the instant disclosure, any of the electrodes discussed are understood to be dual purpose electrodes, both for sensing biometric input from the human body as well as for delivering an electric pulse/shock to the human body, unless otherwise specified. Electrodes (and housing units) that are in direct contact with the user (as opposed to be fitted into a wearable garment), are adhered to the skin using any medium or apparatus known in the art, for example, the undersurface (surface closest to the skin) of the electrode or housing unit can be lined with a layer of bio-adhesive material.

In another example, the housing unit can be embodied in an adhesive patch. The adhesive patch being formed from a protective and/or functional upper layer and an adhesive lower layer (the adhesive, being on the undersurface of the lower layer). The adhesive may be adapted for a single application, thereafter losing its adhesiveness, or for multiple reapplications before losing adhesive capabilities. In between the upper and lower layers are housed the various functional components discussed elsewhere herein.

The electrodes can also be embodied in an adhesive patch for single use or multiple reapplication. The leads may be integral with the patch or coupled thereto via an electrically conductive mechanical coupling, as known in the art.

Additional, exemplary, innovative configurations are depicted in the figures and discussed hereafter. The depicted configurations are not intended to be limiting in any manner but rather exemplary of the large number of potential configurations that can be implemented.

In summary, there is disclosed heretofore an external personal wearable emergency medical treatment device, including a first housing unit 10 including an control unit for an automatic defibrillator device. At least three electrodes are connected in electrical communication with the housing unit. The electrodes are adapted to be positioned in proximity to/electrical communication with a human body at preselected positions selected for monitoring for heartbeat abnormalities and providing electric pulses to the human body. In embodiments, electrodes are adhered to skin of the human body. In embodiments a first of the at least three electrodes is housed in the first (or only) housing unit. In other embodiments, with additional housing units, two of the electrodes are each respectively housed in the two housing units. More electrodes may be added, with or without housing units.

Figure 4:
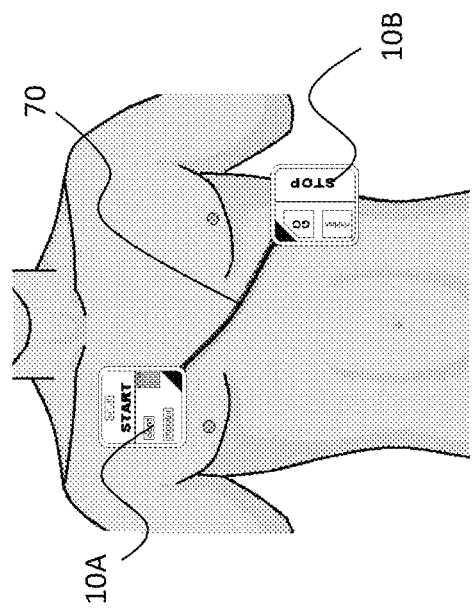
FIG. 4 is a view of a device of an embodiment of the present invention in communication with an additional device.

Device 10 is a multifunctional device. As such, the use of the two devices 10, even in the standard placement configuration (anterior apex), is innovative, as the devices do not only provide monitoring and defibrillating functionality, but also other functions as described here after. FIG. 4 illustrates a first device 10, hereafter device 10A, in electronic and electrical communication with additional device 10, hereafter 10B. A cable equivalent communication 70 is used to separate devices 10, each one of them constitutes an electrode in a system composed of two devices 10 and cable equivalent 70. Since buttons are software selectable, each one of buttons 12, 13, 16 can have a different operation, allowing 18 options of operation in total. Cable equivalent 70 can be used to conduct power in case of defibrillation, or conduct communication between devices 10, or both.

Figure 7:
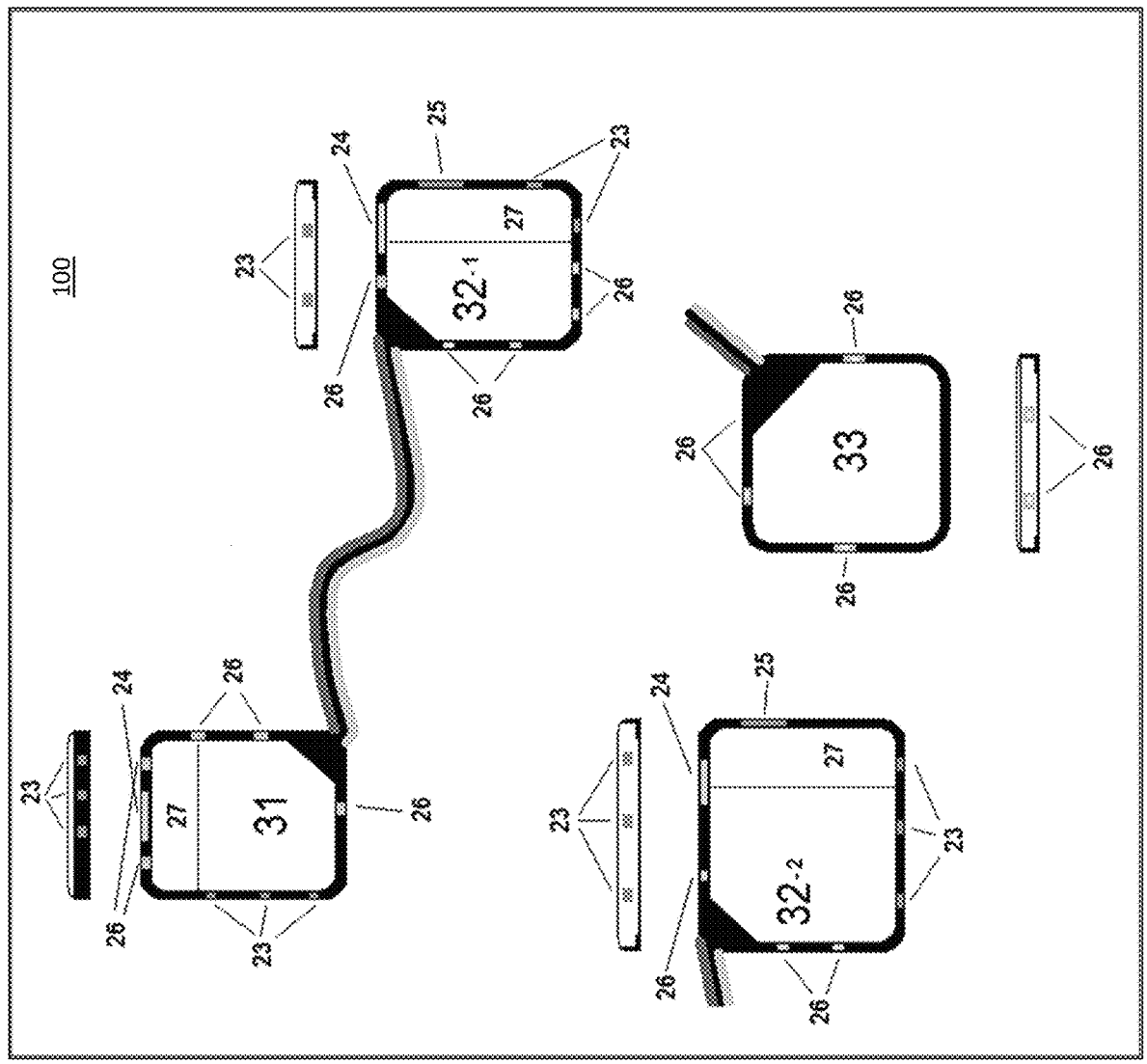
FIG. 7 is a plurality of front and side views of the device of an embodiment of the present invention with additional switches and sockets.

FIG. 7 depicts an exemplary embodiment of system 100 including a plurality of front and side views of the device of an embodiment of the present invention with additional switches and sockets. In one embodiment, the system is comprised of a single housing unit and one or more connected electrodes. In another embodiment, there are one or more additional housing units. Each housing unit contains at least one internal electrode. In the depicted figure, there is depicted a main housing unit, two secondary housing units and a tertiary housing unit. The term housing unit is used in a broad manner throughout the disclosure. In order to specify the aspect of the device relating to the defibrillator functionality, each of the units referred to herein are referred to as electrodes. Each electrode can either be a simple electrode or an electrode with additional components and functionality. Therefore, while the term is inaccurate, it is used herein in a broad manner.

The system 100 consists of units embodied with internal electrodes 31, 32-1, 32-2, 33. Electrodes 31, 32-1 and 32-2 (similar to devices/housing units 10 depicted and detailed elsewhere herein) have on/off submerged switches 23 (visible in the side views of the electrodes) working with a strong press only. In addition electrodes 31, 32-1 and 32-2 each include a connection socket 24 for additional electrodes. Exemplarily electrodes 32-1 and 32-2 have a charging cord socket 25. Electrode 31 may or may not have a charging cord socket (depicted in the figure without). The electrodes each have plug sockets 26 for additional sensors.

As depicted, the main and secondary electrodes have pressing switches 27 which activate a selected operating mode. The main electrode 31 is capable of working without any additional electrodes, however the secondary electrode(s) 32-1/32-2 and electrode 33 (e.g. adapted for posterior positioning, as shown in FIG. 6) cannot function without the main electrode 31. An optional larger electrode 32-2 for storing more energy is disclosed, as well as a back electrode 33 (for GO mode). The GO mode is an automatic mode while a patient is connected to device 10 all day long. This mode is relevant mainly when the patient is at a high risk for sudden cardiac arrest for different reasons and requires constant supervision and monitoring. The system/device 100/10 according to the invention allows the patient to continue a daily routine while being supervised and in case of need treated.

Figure 8:
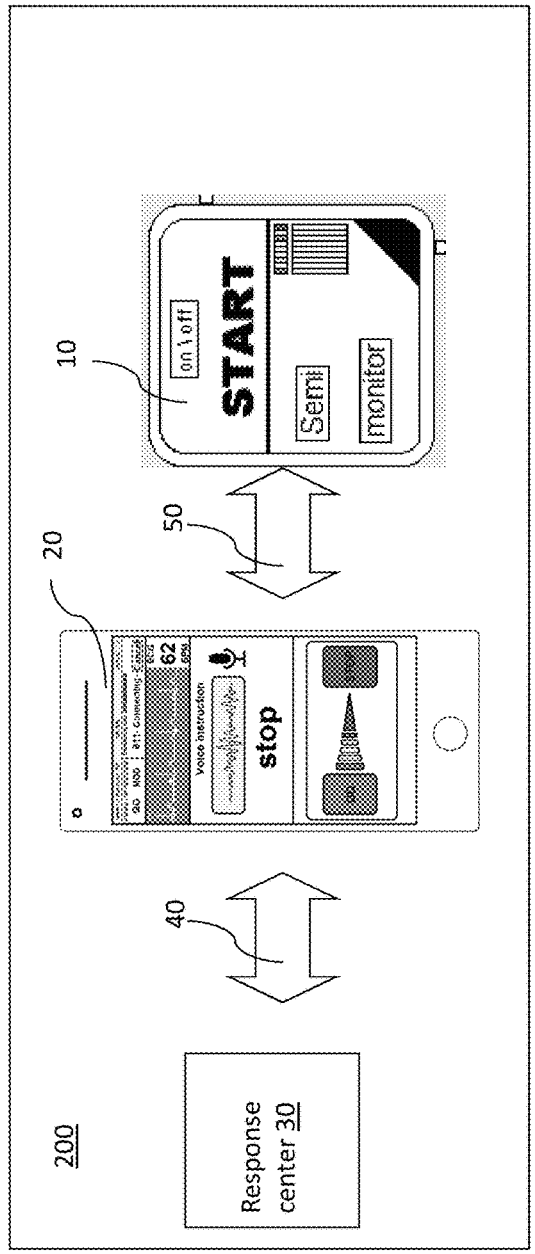
FIG. 8 is a diagram of a system 200.

FIG. 8 depicts a diagram of a system 200. Device 10 includes wireless communications technology housed within housing unit/device 10. Communication 50 is established between device 10 and an external device 20 such as a Smartphone, laptop, tablet, PC, etc. Data from device 10 is presented on the external device 20 screen. The external device 20 can also be used to select modes and configure device 10 using the same communication. Moreover, the external device 20 can also establish communication 40 with a response center 30, and the same data can also be displayed on the response center screens 30. In case the response center 30 has having an on-line caregiver, the caregiver can directly communicate with device 10 via external device 20, change parameters, re-operate device 10, send an emergency response team to a location as advised by the external device 20, either by an internet address, GPS, GPRS data from external device 20, receive audio and video information from patient or by other people standing near the patient, send audio and video information instructions that may be transferred to the patient or by standers in order to provide response as to the status of the patient.

Figure 9:
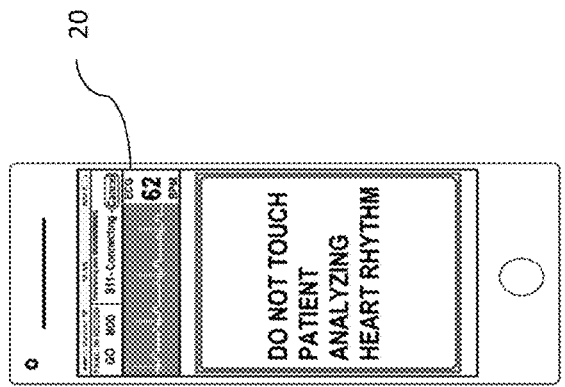
FIG. 9 illustrates a part of an automatic defibrillation procedure according to the present invention.

FIG. 9 depicts a part of an automatic defibrillation procedure, with communication 50 with external device 20, whereby the external device 20 displays a message reflecting the actions required and the status of the device according to a specific situation or indication of the patient, given by the device 10.

Figure 10:
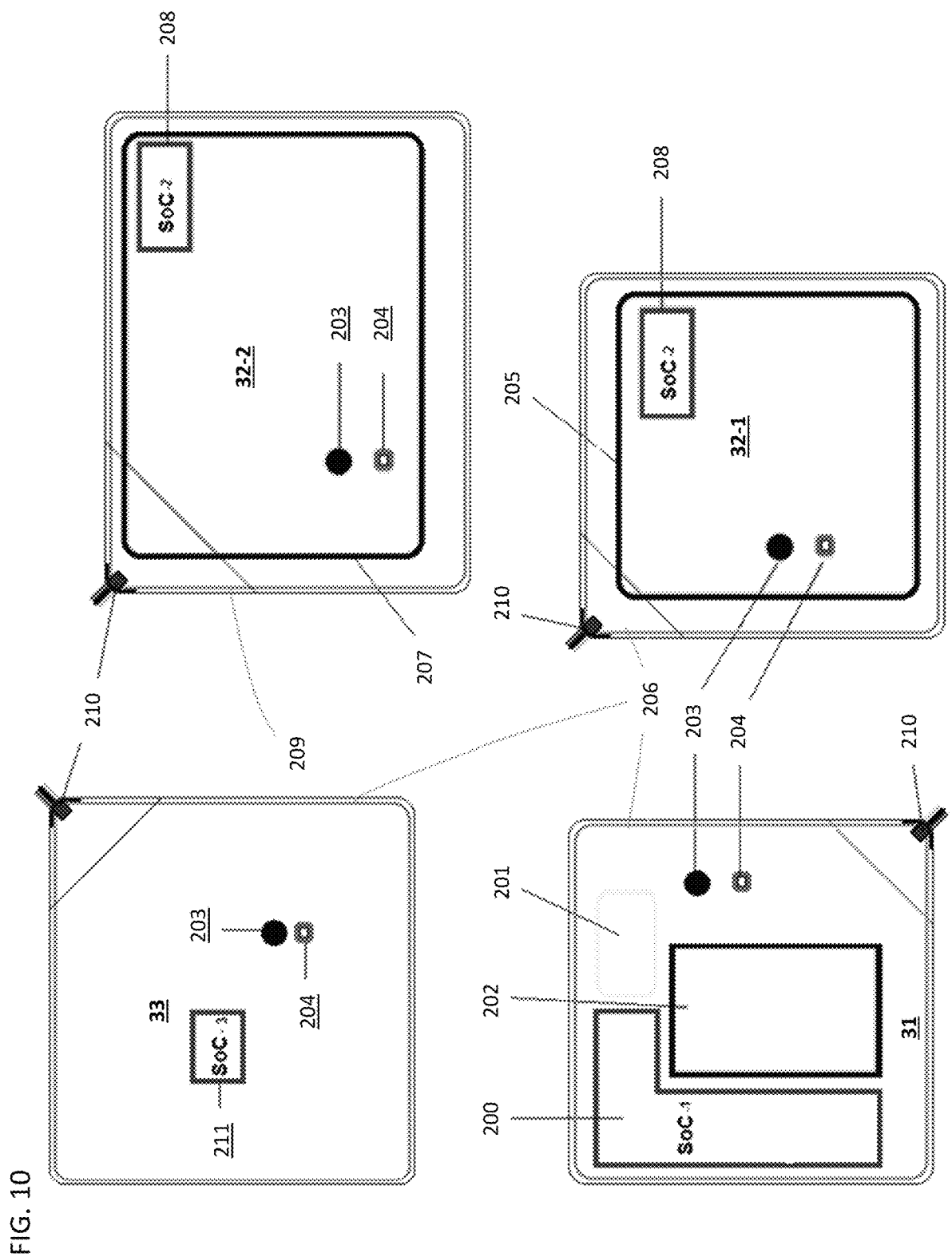
FIG. 10 is a schematic diagram of an exemplary external personal wireless monitored defibrillator aspect of the multifunctional system.

FIG. 10 illustrates a schematic diagram of an exemplary external personal wireless monitored defibrillator aspect of the multifunctional system depicted in FIG. 7 according to the invention. Main electrode 31 includes a main System on Chip (SoC) SoC-1 200, a circuit for data storage unit 201, a main electrode contact 202. All the electrodes have an ECG sensor 203, a temperature sensor 204 and flat cable connectors 210. The main, secondary and back units each have a large area electrode contact 206. Optional secondary electrode 32-2 includes an enlarged area electrode contact 209 for GO mode. The enlarged electrode surface is larger than the electrode contacts of the other units.

Secondary unit-1 has a main battery 205. Optional secondary unit 32-2 has an enlarged battery 207 for GO mode. The enlarged battery is larger than the main battery 205. The secondary devices 32-1 and 32-2 include secondary SoC-2s 208 intended onboard functions of the secondary electrodes. The posterior electrode 33 has a third SoC-3 211 for onboard functioning of the tertiary unit as well as communication with the main and/or secondary units. The SoCs communicate with each other as well as with external devices via wired or wireless means. SoC technology is well known in the art and all components relevant to the functioning of the instant devices as described are to be considered as is set forth fully herein.

Figure 11:
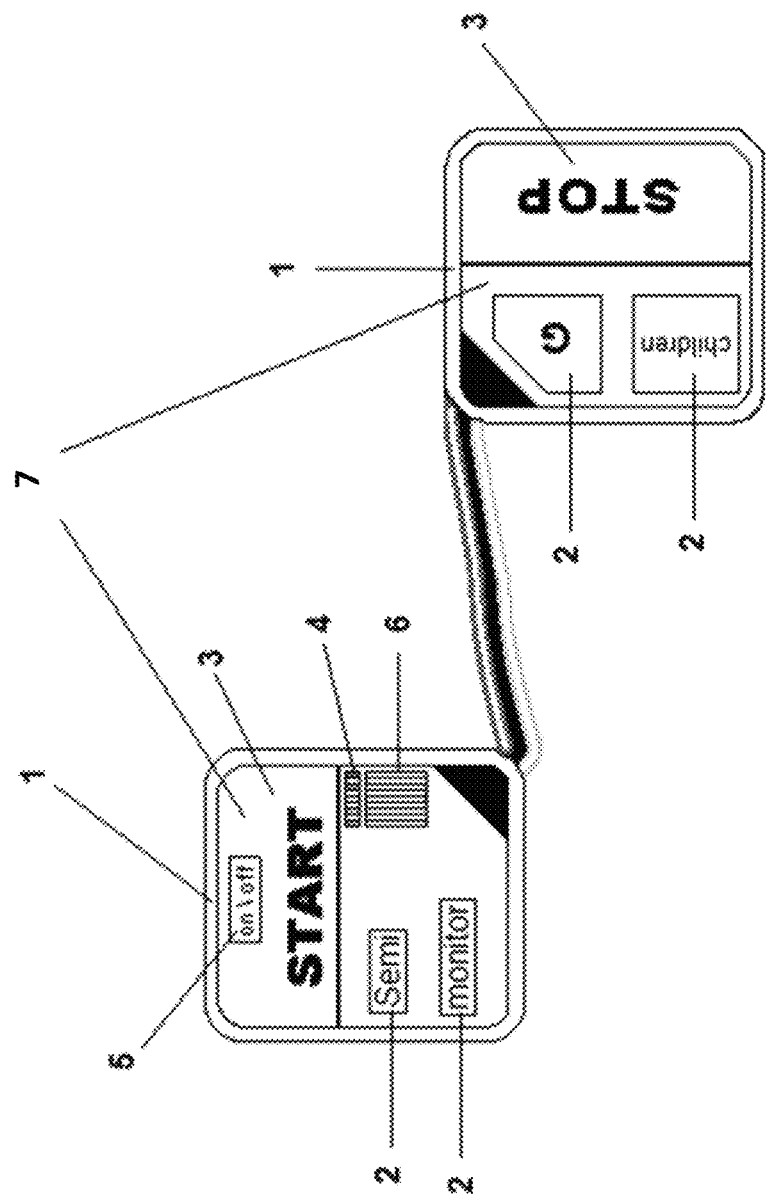
FIG. 11 is a view of the device according to an embodiment of the present invention showing indicator lights, vibration and alarm components.

FIG. 11 depicts two housing units 10. According to an embodiment of the invention, an optional indicator and light alert as well as vibration and audible alarm are depicted in FIG. 11, whereby LED lighting 1 is disposed in the frame of the device and changes color depending on the operation of the device. For example, a green light will signal that CPR can be performed, a red color signals that the device is performing an analysis of the patient, a blinking red indicates that the device is being charged ahead of administering an electric shock and a white flashing light will be displayed during an electric shock.

In addition, there are a plurality of lighting areas 2 that activate to display the device operating mode. A top click button 3 is only active in specific modes. When active, the button will illuminate. An indicator 4 shows the battery status of the device. An indicator 5 shows the general status (On/Off) of the device. In embodiments, the device also includes a speaker 6 for voice alerts and a vibration alert mechanism 7 (not visible).

Figure 12:
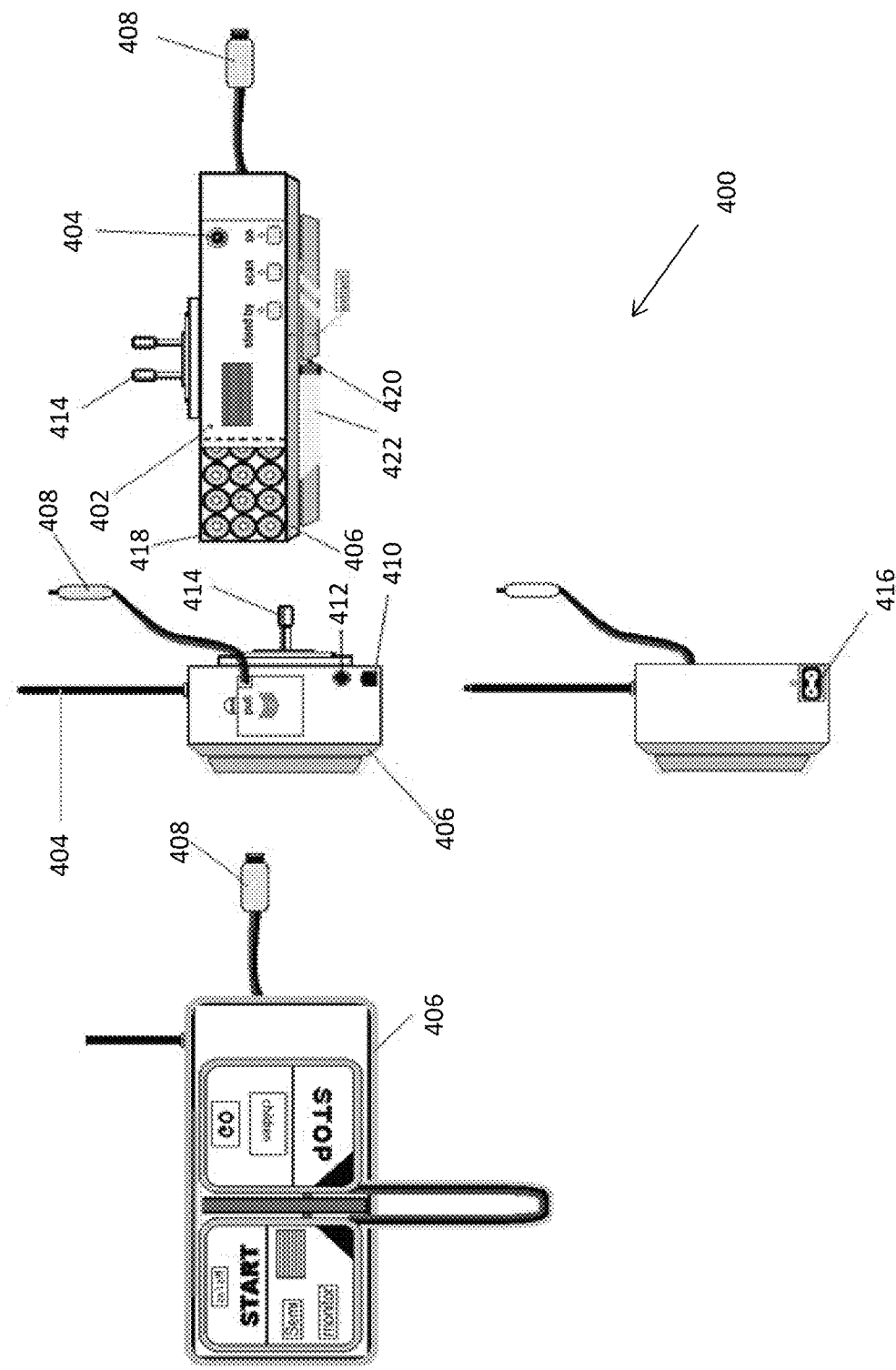
FIG. 12 includes various views of a monitoring and docking station and/or charging station 400.

FIG. 12 depicts various views of a monitoring and docking station and/or charging station 400. According to embodiments, there is disclosed a monitoring and docking station and/or charging station 400, which is used to charge and store device(s) 10. The docking station is used also for a monitoring operation and communication system to and from the device. The station 400 further provides a backup feature in places where there is no communication to the external device 20, such as a smartphone.

In embodiments the monitoring and docking station functions as a router with a wireless communication with the device as well as communication capabilities for passing the data regarding the condition and location of the patient to the rescue center. The latter communication may be accomplished wirelessly or through land lines where such communication is viable. The station includes a speaker 402, a wireless antenna 404, LED lighting 406 as well as a retractable charging cable for GO mode 408. Land line communication socket (telephone) 410 is also available as well as other communication line socket 412, wall plug 414, a power cord socket 416, an emergency battery 418. The station furthermore has a data and charging pin 420 as well as electrode holding mechanism 422.

Figure 13A:
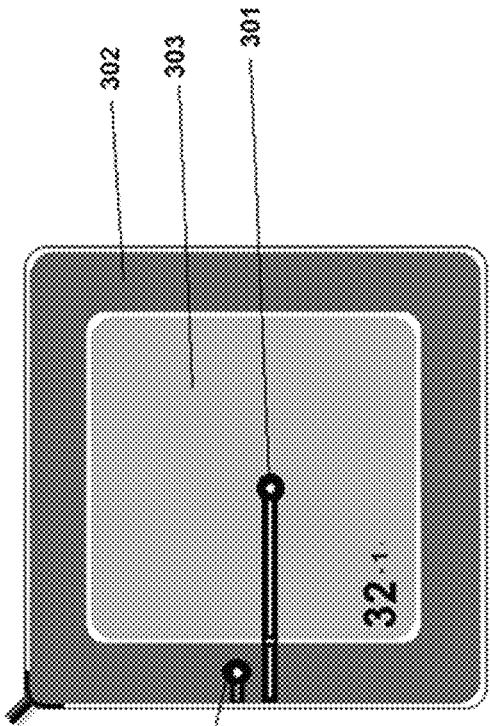
FIGS. 13A and 13B are schematic diagrams of the back view of the electrodes.
Figure 13B:
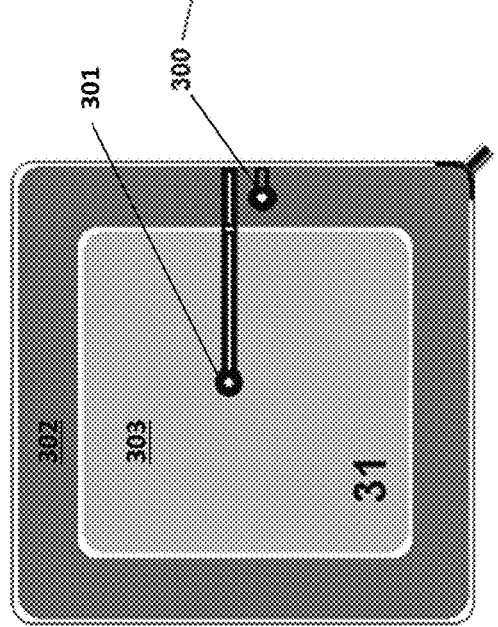

FIGS. 13A and 13B are a schematic diagrams of the back view (inner side—not in contact with skin) of the electrodes in detail. The main and secondary electrodes each have a point of contact 301 in a first, inner shock area 303 from the electrical circuit is shown exemplarily at the middle area of each electrode. A second point of contact 300 is disposed within a second, outer electric shock area 302.

Figure 13C:
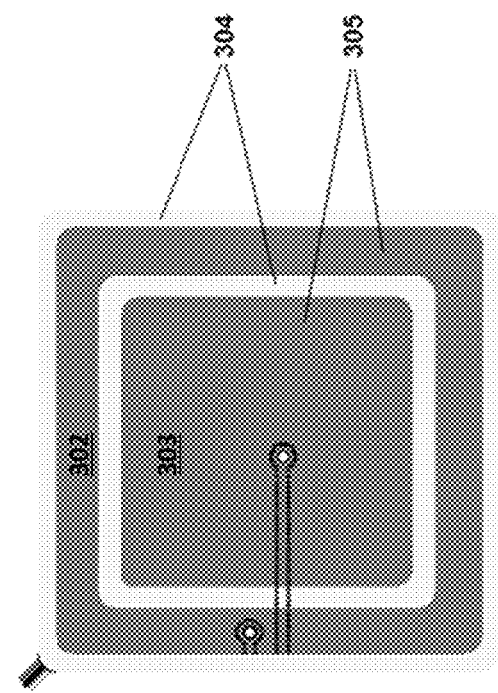
FIG. 13C is a bottom view of an electrode.

FIG. 13C is a bottom view of an electrode, i.e. a view of the underside of the electrode that comes into contact/proximity with the skin. Insulation material 304 and conductive material 305 are disclosed as well. The insulation material forms borders around the shock areas while the conductive material forms the shock areas. Preferably, a conductive gel sticker is attached to, or lines, the underide surface. In "Children Mode" the electric shock will be provided from electric shock outer area 302 only, whereas in other modes the electric shock will be provided from both the inner and outer shock areas 303, 302.

Figure 14:
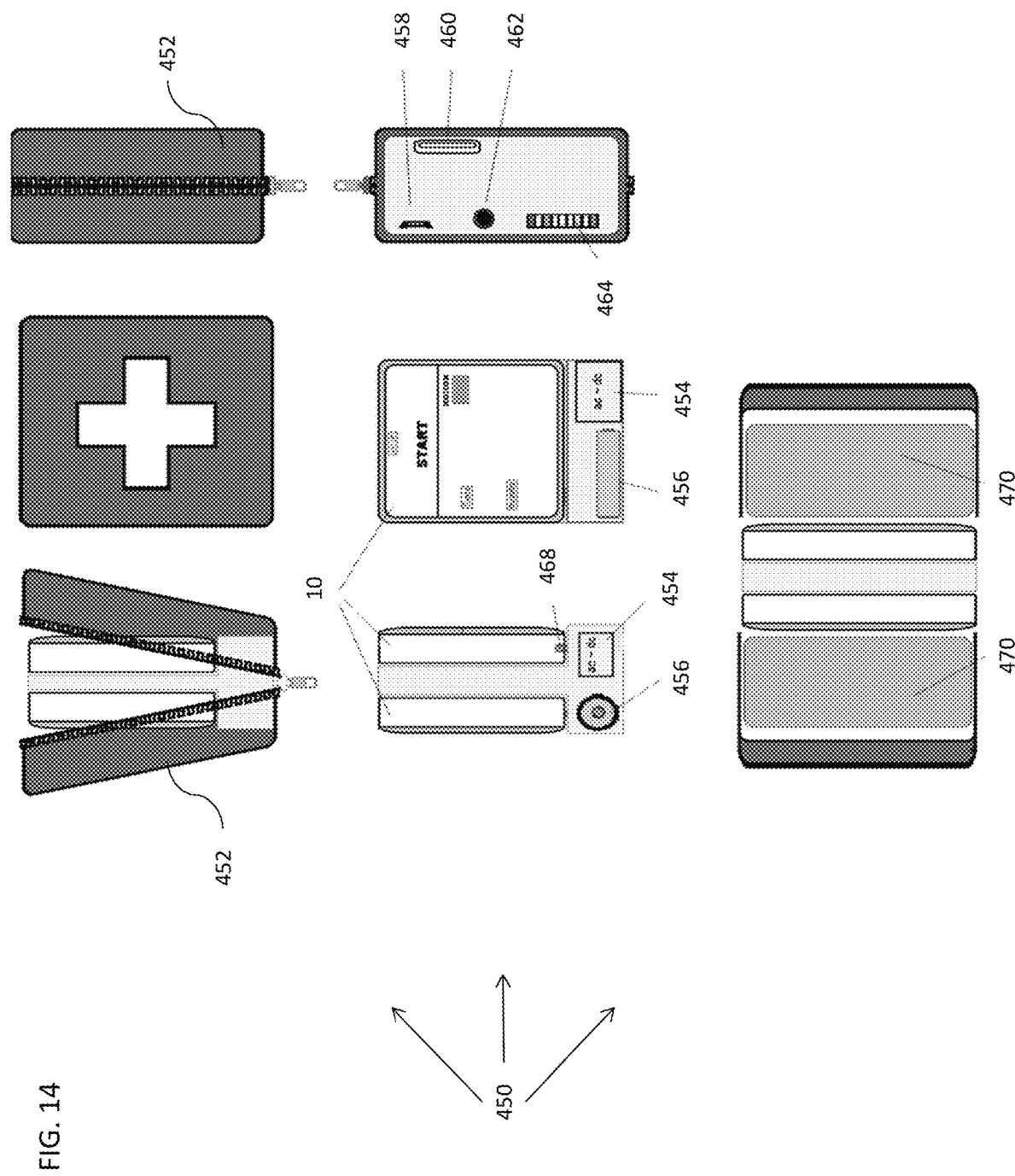
FIG. 14 includes various views of a pouch for carrying the emergency unit.

FIG. 14 depicts various views of a pouch 450 for carrying the emergency unit model. Pouch 450 includes a padded outer cover 452 with a zipper fastener for opening and closing the pouch. The pouch 450 is designed to house two electrodes/housing units 10. The electrodes are docked on a portable platform integrated with the outer cover. The platform has a base and a partition perpendicular to the base. The electrodes are seated or clocked on each side of the partition and rest on the base. The base of the platform optionally includes an AC-DC transformer 454, a backup battery 456. On the underside of the base of the platform is a micro USB-B charging and data socket 458, a USB charging and data socket 460, a charging socket 462 and a charging indictor 464. Two built in charging and data pins 468 protrude from the base one on each side of the partition. Side storage pockets 470 are sewn inside the outer cover 452 and can be used for storing a charging cable and additional patches, and the like.

Another possible configuration is shown in FIGS. 15A, 15B, 15C and 15D. FIG. 15A illustrates a view of the inside of a wearable vest 500. Vest 500 is specially designed to hold three electrodes, such as a main electrode 10A, a secondary electrode 10B and a tertiary 10C discussed above. The electrodes/housing units/devices 10 are removably inserted into the vest. A cable 70 connects between the units. In the depicted figure, various leads 17 are connected to the units. The leads may function to gather ECG sensor readings (e.g. as arranged in an Einthoven triangle) and/or respiration rate and/or temperature as discussed above. Some leads may additionally or alternatively be configured for providing an electric shock, as discussed above.

It is made clear that the design of the vest and the number of units inserted therein is merely exemplary and not intended to be limiting. Vest designed for more or less units are considered within the scope of the invention. Some units may be multifunctional housing units while other may be simple electrodes with minimal or no additional components.

It is further made clear that any embodiment, variation, component, configuration etc. that has been mentioned herein is intended to apply to all other configurations, embodiments, alternates etc. Therefore, none of the embodiments mentioned herein are intended to limit the scope of the invention but rather to enlarge that scope. If one component is depicted and detailed with regards to a given embodiment, it is made clear that that component is considered to be an optional part of any other embodiment, mutatis mutandis, where relevant. Once a component has been mentioned herein, it is to be considered as if that component has been fully detailed, mutatis mutandis, for every other relevant embodiment.

Keeping within the generalization detailed heretofore, FIGS. 15B, 15C and 15D depict optional embodiments of the vest 500, as worn on a body. FIG. 15B depicts a main or first housing unit 10A in the anterior position and a second or secondary unit 10B in the apex position, presenting the standard anterior-apex scheme. FIG. 15c depicts a third or tertiary unit on the back of the vest, positioned between the scapula in the posterior position. FIGS. 15B and 15C mirror electrodes and positions depicted in FIG. 6. FIG. 15D depicts a secondary unit positioned in a location that corresponds to the side of the body. The main unit may be placed on the other side of the body (not shown) in an alternate, or additional, configuration (the side-to-side configuration) to the configuration of FIG. 15B or FIGS. 15B and 15C.

In summary, the electrodes discussed elsewhere herein are inserted into a garment adapted to be worn on a human body such that the electrodes are in proximity to, and hence in position to be in electrical communication with, the human body wearing the garment.

Figure 16:
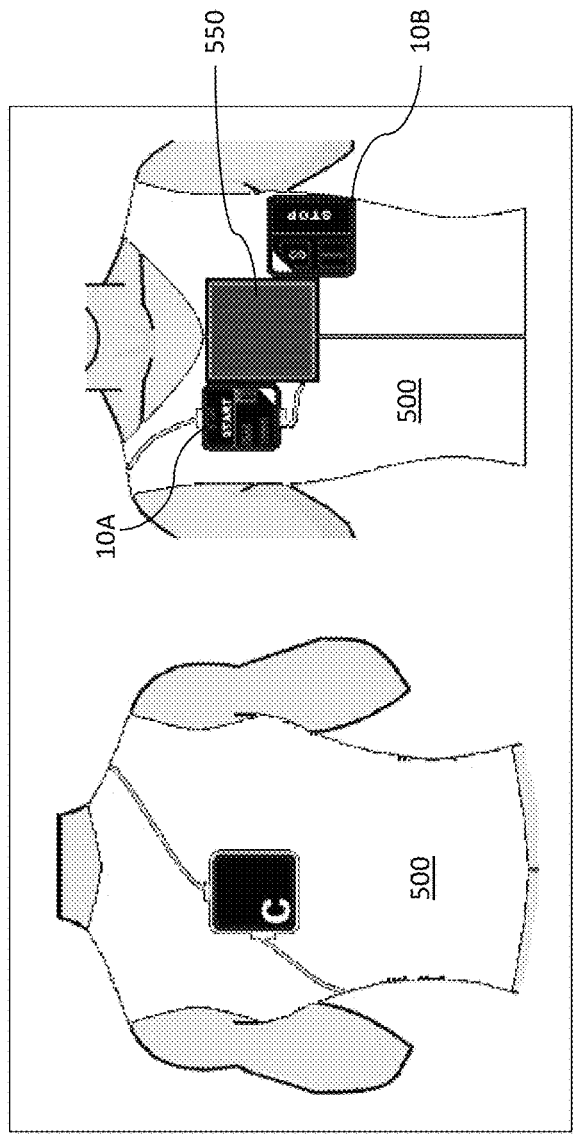
FIG. 16 is a view of an embodiment of the personal wearable emergency medical treatment device including ultrasound functionality.

Yet another configuration is shown in FIG. 16 which depicts an embodiment of the personal wearable emergency medical treatment device including ultrasound functionality. A unique function and another means of monitoring for the patient and for the caregiver is the possibility of performing a cardiovascular ultrasound examination through the personal medical device. The ultrasound patch 550 is provided in a dedicated location and a module (e.g. a dedicated SoC or the SoC housed in one of the housing units) processes the ultrasound data obtained from the sensors scanning the patient.

As with all data gathered from the personal medical device, the processed information received from the device can be transmitted, upon request, on-line and/or in real time to a remote patient physician, as part of a telemedicine interaction. The data can, additionally or alternatively, be sent to the medical file located on a server/cloud for later viewing. Alternatively or additionally, the data is stored in a personal medical record in memory on the device. In embodiments, the information can be seen via the app on the smartphone 20.

The aforementioned procedure can be performed in any of two ways (Multi-functional), one general and the other personal: On a general level, in places where medical devices are ubiquitous (e.g. hospitals, nursing homes, hostels, clinics and ambulances) it makes sense to use an existing ultrasound probe (wired or wireless) plugged into or otherwise connected to the instant device, even if the probe is manufactured by different manufacturers than the instant device.

The second way entails a personalized approach. Patients who require permanent ultrasound examinations on demand, or as requested by the patient, mount a transducer in the personal medicine device, either directly on the skin or in the vest. Specifically, a flexible ultrasound patch can be coupled, in a wired or wireless manner, to the housing unit. The patch may be specifically manufactured or sourced from other manufacturers.

FIG. 16 depicts a vest 500 as illustrated in FIGS. 15B and 15C, but with the addition of an ultrasound patch 550. In one embodiment, as depicted, the patch is inserted in (or otherwise attached to) vest 500. In another embodiment, the patch 550 is adhered directly to the skin of the user in a similar way to that which has been detailed elsewhere herein for other components.

As mentioned elsewhere herein, the fact that, the instant exemplary embodiment is described in relation to a specific selection and arrangement of components does not limit the application of the instant functionality to the depicted and detailed embodiment. Rather, the ultrasound functionality is intended to be applied to all embodiments and configurations mentioned herein and the variations thereof that would be obvious, after learning the instant disclosure, to one skilled in the art.

One implementation of a flexible ultrasound probe is a thin patch of silicone elastomer patterned with what is called an "island-bridge" structure. This is essentially an array of small electronic parts (islands) that are each connected by spring-like structures (bridges). The islands contain electrodes and piezoelectric transducers, which produce ultrasound waves when electricity passes through them. The bridges are spring-shaped copper wires that can stretch and bend, allowing the patch to conform to non-planar surfaces without compromising electronic functions. According to another implementation, the piezoelectric crystals are replaced with tiny vibrating drums made of polymer resin, called polyCMUTs (polymer capacitive micro-machined ultrasound transducers), which are cheaper to manufacture.

Another feature of the multi-functional personal medical device is the ability to provide a life-saving medication in an emergency situation. The instant housing unit has the technological ability to interface with various other devices and sensors. Accordingly, the instant innovation provides an additional resuscitation device over an AED or WCD (wearable cardioverter defibrillator). The personal medical device or suite operates on two levels: on one level the system provides an external electric shock (defibrillation or cardioversion) and on another level the device provides an emergency medication to the patient. The combination of electrical shock and automatically administered medication increases the patient chances of surviving the event.

Figure 17:
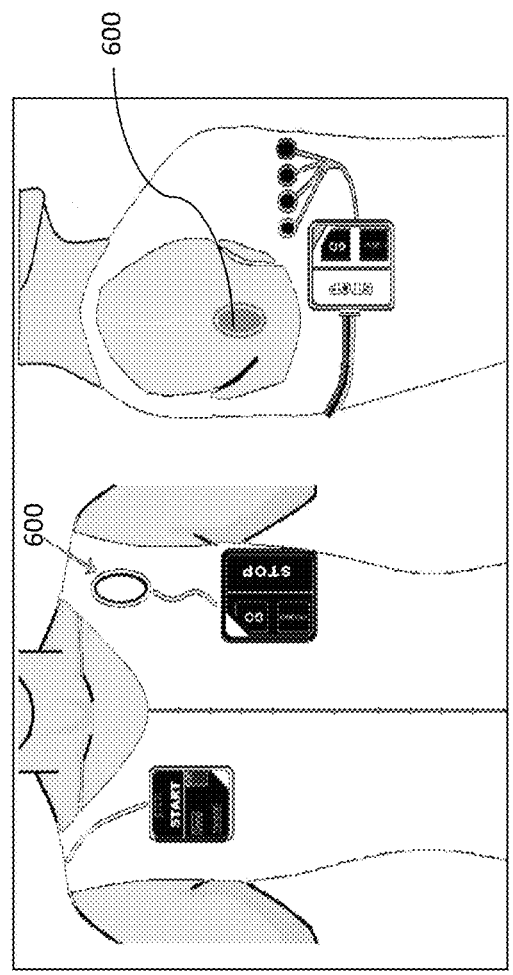
FIG. 17 is a view of two exemplary applications of an emergency medicine patch on a body.

FIG. 17 illustrates two exemplary applications of an emergency medicine patch on a body. "Emergency Patch" 600 is a unique resuscitation device that can be added to a personal wearable medical device suite, in the form of an external patch having therein a wearable/on-body injector that is synchronized with the main housing unit. The patch can be controlled wirelessly or via a connecting cable by the main housing unit.

Figure 18:
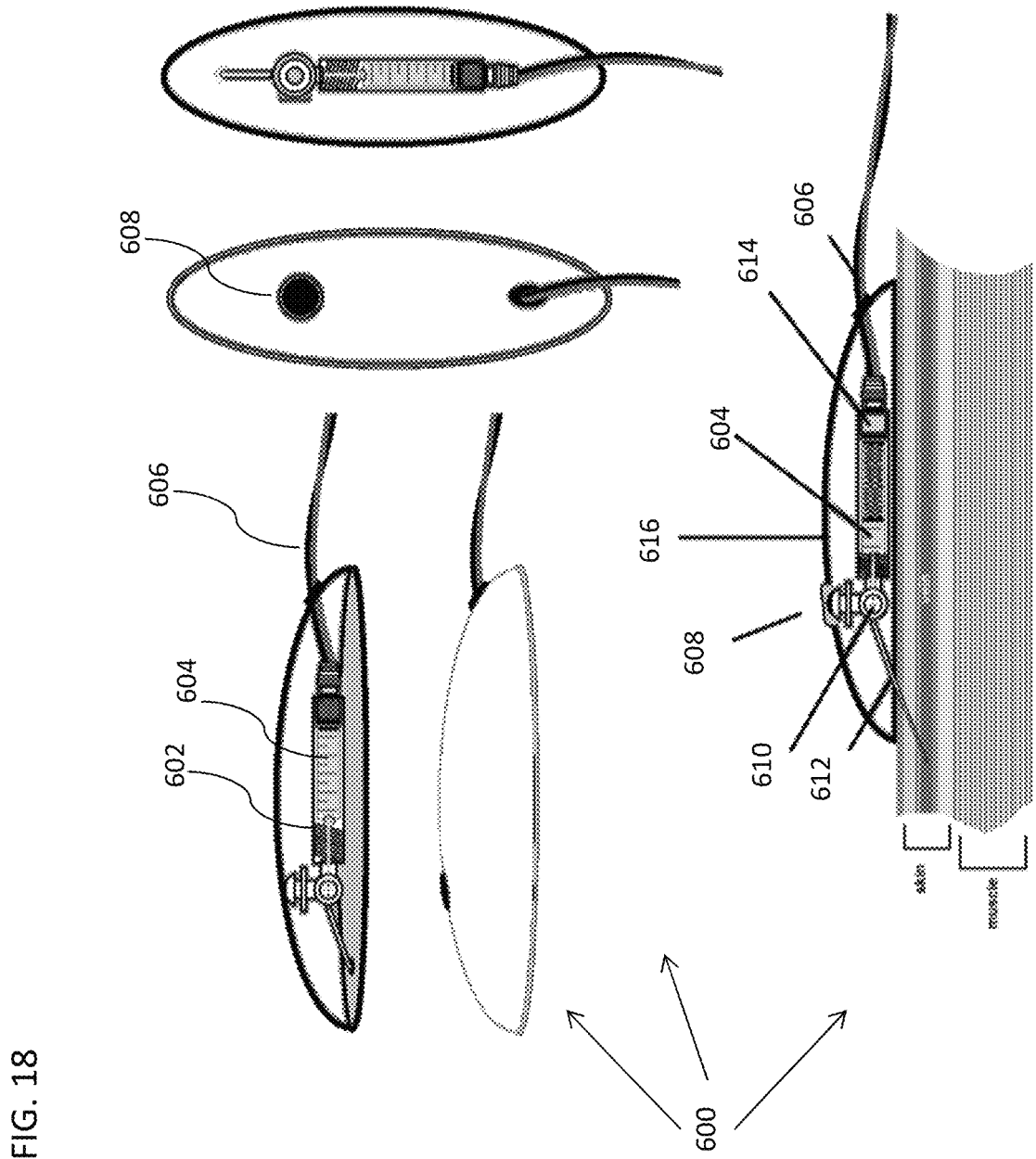
FIG. 18 includes various views of the emergency patch.

FIG. 18 depicts various views of the emergency patch 600. An electromechanical syringe 602 is housed within the patch 600 containing a measured amount of patient-specific emergency medicine 604 (e.g. based on weight, known allergies, disease, etc.). This patch/drug will be provided as required by the caregiver (physician) according to the patient's medical needs and condition. The patch 600 connects (in a wired configuration) to the main housing unit (or other housing unit with a SoC) that is configured to control the actuation of the patch via a cable or lead 606. The medicament can be injected incrementally over a period of time or all at once. The injection can be manually actuated via a push button 608. The push button is mechanically coupled to a valve 610 disposed between the syringe body and a needle 612. Exemplarily, the control unit actuates a solenoid 614 which opens (expands) to expel the medicament from the syringe. A padded upper cover 616 covers over the internal components of the patch, providing some protection to those components. The internal contents are sandwiched between the upper cover 616 and bottom layer 618 that lies against the skin. An adhesive lines the underside of the bottom layer, adhering the patch to the skin.

Future medical research will determine the precise protocol for combined CPR/defibrillation and emergency drug injection, since the parameters for such an integrated, automatic operation in the field of External Medical Cardiology Emergency Equipment are heretofore unknown as no such automated integrated system has been developed until now.

The "Emergency Patch" is employed as part of the GO operating mode where the patient wears the personal wearable medical device on his or her body throughout the day.

In fact, in the case of an emergency PWMD, the device can offer any emergency and non-emergency medication so long as the developing medical condition or event can be monitored and analyzed with the various sensors and devices (also from other manufacturers). The patch can be applied externally or subcutaneously or via intravenous injection. Parameters for an expected medical event can be preprogrammed on the PWMD.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A personal wearable emergency medical treatment device, comprising:
   (a) a first housing unit including a control unit for an automatic defibrillator device;
   (b) at least three electrodes in electrical communication with the housing unit;
   wherein said electrodes are adapted to be positioned in proximity to a human body at preselected positions selected for monitoring for heartbeat abnormalities and at least three of said electrodes are adapted to provide electric pulses from the automatic defibrillator device to said human body, wherein said electric pulses are electric shocks in a range between 50 and 400 Joules and wherein each of said at least three electrodes is configured to deliver electric shocks of different magnitudes during a single event.

2. The device of claim 1, further comprising a fourth electrode in electrical communication with said housing unit and adapted to provide said electric pulses or adapted to provide said electric pulses and additionally monitor for said heartbeat abnormalities.

3. The device of claim 1, wherein one of said at least three electrodes is housed in said first housing unit.

4. The device of claim 1, further including at least one additional housing unit, and wherein at least two of said at least three electrodes are each respectively housed in said housing units.

5. The device of claim 1, wherein said at least three electrodes are inserted into a garment adapted to be worn on said human body such that said electrodes are in proximity to said human body.

6. The device of claim 1, further comprising a flexible ultrasound probe in electrical communication with said housing unit.

7. The device of claim 1, further comprising an emergency medicine patch in electrical communication with said housing unit, said patch including a syringe, a needle mechanically coupled to said syringe, said syringe adapted to store therein a medicament; and an actuator for expelling said medicament via said needle upon actuation by a signal sent from said housing unit.

8. The device of claim 2, wherein said housing further includes at least a portion of:
   at least one electrode of said at least three electrodes for capturing cardiac signal data,
   the control unit having an electrical circuit, said circuit including a controller, data storage, and input ports, said electrical circuit being designed to read inputs and to store data,
   a plurality of sensors connected to said electrical circuit inputs,
   a communication port, for uploading and downloading data to other devices having a communication port, and
   an operating software, analyzing the captured cardiac signal data to determine whether a treatable cardiac arrhythmia is occurring.

9. The device of claim 8, wherein the device is configured to:
   detect a cardiac event by observation of electrical signals captured using at least some of the electrodes;
   calculate a cardiac event rate relative to the detected cardiac event;
   analyze a correlation of the cardiac event relative to teachable patient cardiac output; and
   determine that the cardiac event has correlation to the teachable patient cardiac output and deliver said electric pulses.

10. The device of claim 2, wherein the device is configured to be in wireless or wired communication with an external device.

11. The device of claim 8, further comprising selectable dual functions, automatic and semi-automatic functioning modes.

12. The device of claim 8, wherein the device is configured to be charged and for multi-use.

13. The device of claim 1, wherein the device is for a plurality of operating modes.

14. The device of claim 13, wherein the operating modes include at least the modes of emergency, detection, children, and wearable.

15. The device of claim 14, wherein the wearable mode is a Go-Mode, intended for 24 hours wearing of the device on the patient body.

16. The device of claim 1, wherein the device is configured to be modular and is capable to be connected to at least one of: additional electrodes, additional sensors, and additional devices.

17. The device of claim 1, wherein the device is personally configurable according to a patient's medical information.

18. The device of claim 10, wherein the device is capable of wirelessly receiving protocol updates direct from said external device.

19. The device of claim 10, further comprising an application to be downloadable by the external device or from the internet.

20. The device of claim 1, wherein said electric pulses are electric shocks and wherein the device is configured to deliver electric shocks of different magnitudes.

21. The device of claim 8, wherein the device is configured to measure body indications selected from the group including: temperature, heart rate, respiration rate, and blood sugar ranges.

22. The device of claim 21, wherein measuring the blood sugar ranges is done by an additional sensor connected to the device.

23. The device of claim 1, wherein at least one of said electrodes has a different size relative to at least one other electrode, intended for a different shock magnitude.

24. The device of claim 14, wherein the at least one of said electrodes is intended for wearable mode and at least one of the electrodes is intended for emergency mode.

25. The device of claim 1, further comprising light, voice and vibration indicators.

26. The device of claim 1, wherein said electrodes comprise a wearable patch adapted to be adhered to skin of said human body.

27. A pouch for carrying the device of claim 1, further comprising a charging port.

28. The pouch of claim 3, further comprising a transformer, a battery, charging sockets and indicators.

29. A monitoring and docking station comprising: a charging station, a communication system and a backup battery adapted for use with the device of claim 1.

30. The monitoring and docking station of claim 29, wherein the monitoring and docking station further includes wide area wireless communication capabilities.

31. The device of claim 1, wherein a first electrode passes a first pulse to said third electrode and a second electrode passes a second pulse to said third electrode during a single defibrillation event, wherein said first and second pulses are passed simultaneously or consecutively.

32. The device of claim 2, wherein said electric pulses flow from a first electrode to a second electrode, from said second electrode to said third electrode and from said third electrode to said fourth electrode and from fourth electrode to said first electrode during a single defibrillation event.

33. A personal wearable emergency medical treatment device, comprising:
- (a) a first housing unit including a control unit for an automatic defibrillator device;
- (b) at least three electrodes in electrical communication with the housing unit;
- wherein said electrodes are adapted to be positioned in proximity to a human body at preselected positions selected for monitoring for heartbeat abnormalities and at least three of said electrodes are adapted to provide electric pulses from the automatic defibrillator device to said human body, wherein a first electrode passes a first pulse to a second electrode and a second electrode passes a second pulse to said third electrode and said third electrode passes a third pulse to said first electrode during a single defibrillation event, wherein said first, second and third pulses are passed simultaneously or sequentially.

34. A personal wearable emergency medical treatment device, comprising:
- (a) a first housing unit including a control unit for an automatic defibrillator device;
- (b) at least three electrodes in electrical communication with the housing unit;
- wherein said electrodes are adapted to be positioned in proximity to a human body at preselected positions selected for monitoring for heartbeat abnormalities and at least three of said electrodes are adapted to provide electric pulses from the automatic defibrillator device to said human body, wherein said electric pulses flow reciprocally from a first electrode to a second electrode, from said second electrode to said third electrode, and from said third electrode to said first electrode during a single defibrillation event.

* * * * *